US007118861B1

(12) United States Patent
Naaman et al.

(10) Patent No.: US 7,118,861 B1
(45) Date of Patent: Oct. 10, 2006

(54) DNA DETECTOR BASED ON MOLECULAR CONTROLLED SEMICONDUCTOR RESISTOR

(75) Inventors: Ron Naaman, Ness Ziona (IL); David Cahen, Rehovot (IL); Reit Artzi, Tel-Aviv (IL)

(73) Assignee: Yeda Research and Development Co., Ltd., Rehovet (IL)

( * ) Notice: Subject to any disclaimer, the term of this patent is extended or adjusted under 35 U.S.C. 154(b) by 602 days.

(21) Appl. No.: 10/009,167

(22) PCT Filed: Jun. 7, 2000

(86) PCT No.: PCT/IL00/00333

§ 371 (c)(1),
(2), (4) Date: Jun. 5, 2002

(87) PCT Pub. No.: WO00/75276

PCT Pub. Date: Dec. 14, 2000

(30) Foreign Application Priority Data

Jun. 7, 1999 (IL) .................................. 130326

(51) Int. Cl.
*C12Q 1/68* (2006.01)
*G01N 33/00* (2006.01)
*H01L 51/00* (2006.01)
(52) U.S. Cl. ................ 435/6; 436/94; 257/40
(58) Field of Classification Search ............ 435/6; 257/40
See application file for complete search history.

(56) References Cited

U.S. PATENT DOCUMENTS

| 4,238,757 A | 12/1980 | Schenck |
| 5,556,529 A | 9/1996 | Nemoto |
| 5,632,957 A * | 5/1997 | Heller et al. ............. 422/68.1 |
| 5,776,672 A * | 7/1998 | Hashimoto et al. ........... 435/6 |
| 5,837,832 A * | 11/1998 | Chee et al. ............... 536/22.1 |
| 5,945,832 A * | 8/1999 | Harvey et al. ............. 324/693 |
| 6,251,685 B1 | 6/2001 | Dorsel et al. |

FOREIGN PATENT DOCUMENTS

| WO | WO 98/19151 A1 | 5/1998 |
| WO | WO 9819151 A1 * | 5/1998 |

OTHER PUBLICATIONS

K. Gartsman et al., "Molecular Control of a GaAs Transistor", *Chemical Physics Letters*, Feb. 13, 1998, vol. 238, pp. 301-306.
A. Vilan et al., "Real-Time Electronic Monitoring of Adsorption Kinetics: Evidence for Two-Site Adsorption Mechanism of Dicarboxylic Acids on GaAs(100)", *The Journal of Physical Chemistry B*, Apr. 30, 1998, vol. 102, No. 18, pp. 3307-3309.

* cited by examiner

*Primary Examiner*—Kenneth R. Horlick
*Assistant Examiner*—Christopher M. Babic
(74) *Attorney, Agent, or Firm*—Browdy and Neimark, PLLC (57) ABSTRACT

A semiconductor device for the detection of a target DNA or RNA is provided, composed of: at least one insulating or semi-insulating layer; one conducting semiconductor layer; two conducting pads on the upper layer making electrical contact with the conducting semiconductor layer, such that electrical current can flow between them at a finite distance from the surface of the device; and a layer of at least one single-stranded DNA probe directly adsorbed on the surface of the upper layer which is either a conducting semiconductor layer or an insulating or semi-insulating layer. The DNA probe may have a sequence complementary to a sequence of the target DNA or RNA, e.g., a sequence of a gene responsible for a genetic disease or disorder, and the detection of the target DNA is carried out by hybridization with the probe and monitoring either the current change resulting from the hybridization process when a constant electric potential is applied between the two conducting pads or measuring the change in the electric potential required to keep a constant current.

16 Claims, 6 Drawing Sheets

DNA DETECTOR BASED ON MOLECULAR CONTROLLED SEMICONDUCTOR RESISTOR

REFERENCE TO RELATED APPLICATIONS

The present application is the national stage under 35 U.S.C. 371 of international application PCT/IL00/00333, filed Jun. 7, 2000, which designated the United States, and which international application was published under PCT Article 21 (2) in the English language.

FIELD OF THE INVENTION

The present invention relates to DNA detectors, and more particularly to a detector of DNA and RNA sequences and DNA mutations, based on molecular controlled semiconductor resistors.

BACKGROUND OF THE INVENTION

Deoxyribonucleic acid (DNA) is the genetic information carrier found predominantly in the nucleus of living cells and constitutes the primary genetic material of all cellular organisms and of DNA viruses.

DNA is a linear or circular double-stranded helical polymer, each strand containing a sugar-phosphate backbone composed of deoxyribose sugar moieties substituted by phosphate groups at their 5' and 3' hydroxyls, the sugar groups being connected to 4 purine and pyrimidine bases usually indicated by their initial letters, namely, adenine (A), guanine (G), cytosine (C) and thymine (T). The two single strands of the DNA (ssDNA) are connected through hydrogen bonds between the complementary base pairs A-T and C-G (the Watson-Crick base pairs), of the two strands.

Genes are segments of DNA molecules containing all the information required for synthesis of a product, namely, a protein/polypeptide chain with a certain biological function or an RNA molecule. A mutation in a gene, e.g., a change in one or more base pairs of the normal gene, may result in a protein product with a change in biological function and, thus, in a genetic defeat or disease.

In the biological process of synthesis of polypeptide chains, the first step is transcription whereby the double-stranded DNA (dsDNA) serves as a template for synthesis of a single-stranded ribonucleic acid (RNA) with a base sequence complementary to one strand of the double-stranded DNA. In the second step, the translation, the polypeptide chain is synthesized using the RNA as a template. The amino acid sequence of the protein is completely determined by the sequence of bases in the RNA, which in turn is determined by the sequence of bases in the DNA of the gene from which it was transcribed.

The two single strands constituting a double-stranded DNA (dsDNA) can be separated by heating the DNA to ~90° C. or by increasing the pH to extreme values, in a process called denaturation. The denatured complementary strands can react again to form the dsDNA by slow cooling of the DNA to the body temperature or by reducing the pH back to neutral, in a process called hybridization.

The hybridization process provides a powerful technique to detect mutations in a DNA sequence due to the selective binding of a single-stranded DNA (ssDNA) to its complementary strand. This specific property of the DNA is referred to as the "recognition" process.

The selectivity of the hybridization is affected by the conditions in which this process is done, i.e., the solvent (ionic strength) and the temperature. It is expected that the hybridization kinetics will depend on the number of complementary bases. The difference in hybridization rates, when the number of complementary bases changes, is an indication of the selectivity of the process.

Fast and efficient determination of DNA sequences and, particularly, the identification of mutations occurring in DNA sequences, is of major importance in the diagnosis of genetic diseases and in certain cases of cancer.

Several methods have been developed in recent years for the detection and isolation of specific DNA sequences, for example for diagnostic applications. Some of these methods are based on molecular hybridization whereby formation of a partially or fully complementary nucleic acid duplex occurs by association of single strands, usually between DNA and RNA strands, but also between RNA strands. In the technique of in situ hybridization, a known nucleic acid sequence, single stranded and usually with radioactive or fluorescent labels, is applied to a DNA-containing sample and annealing occurs in situ.

Conventional techniques exist for automated DNA sequencing and mutation detection. However, some of these methods include radioactive labeling, which require special handling techniques. In addition, obtaining results using the old methods may take several days. The computerized methods with similar principles are faster but expensive.

The sensors that are currently used for mutation detection are usually based on a probe ssDNA that is immobilized on a substrate, which can be silicon, polymer, gold, etc. The substrate is connected to a transducer that translates the signal of the events occurring on the surface into a physically measurable parameter. The addition of the target DNA and its level of hybridization to different probes on the substrate is indicated by a change in the signal. The hybridization between two fully complementary strands yields a change in the signal, that should be distinguished significantly from the hybridization between two non-complementary or partially complementary strands.

The currently developed detectors can be categorized according to the detection methods they use. Electrochemical-, fluorescent- and transistor-based detectors are known wherein the first step in their development is the immobilization process, in which a DNA strand is connected to a substrate.

One example of DNA sensors, based on fluorescence detection, is described by Nemoto et al. (U.S. Pat. No. 5,556,529) or by Livache et al., 1994. In that method, DNA sequences are amplified by replication for better sensitivity and then transcribed to double-stranded RNA. The synthesis of double-stranded RNA is quantified by fluorescence.

A second example of DNA sensors is electrochemically-based (Wang et al., 1996), in which a single-stranded DNA, which is adsorbed on an electrode, reacts with a complementary strand and the reaction is monitored by chronopotentiometric measurements.

Another detection method of biological reactions is based on the use of a field effect transistor (Schenk, U.S. Pat. No. 4,238,757) whereby the current between two electrodes in a silicon-based transistor is measured as a function of the voltage on a third electrode inserted in a biological solution, which is placed in the gap between the two electrodes.

PCT Publication No. WO 98/19151 (Cahen et al., 1998), of the same applicants of the present application, herein incorporated by reference as if herein described in its entirety, describes a hybrid organic-inorganic semiconductor device and sensors based thereon, said device characterized by being composed of:

(i) at least one layer of a conducting semiconductor;

(ii) at least one insulating layer;

(iii) a multifunctional organic sensing molecule directly chemisorbed on one of its surfaces, said multifunctional organic sensing molecule having at least one functional group that binds to said surface and at least one other functional group that serves as a sensor; and (iv) two conducting pads on the top layer making electrical contact with the electrically conducting layer (i), such that electrical current can flow between them at a finite distance from the surface of the device.

These molecular controlled semiconductor resistors, herein designated MOCSER, are hybrid organic-inorganic semiconductor devices composed of one or more insulating or semi-insulating layers, one conducting semiconductor layer, two conducting pads, and a layer of multifunctional organic molecules, characterized in that: (i) said conducting semiconductor layer is on top of one of said insulating or semi-insulating layers; (ii) said two conducting pads are on both sides on top of an upper layer which is either said conducting semiconductor layer or another of said insulating or semi-insulating layers, making electrical contact with said conducting semiconductor layer; and (iii) said layer of multifunctional organic molecules is directly bound through at least one of said functional groups to the surface of said upper layer, between the two conducting pads, and at least another of said functional groups of said multifunctional organic molecules binds chemicals or absorbs light. The multifunctional organic molecules are directly bound to the surface of said upper conducting semiconductor layer or insulating or semi-insulating layer through at least one functional group selected from one or more aliphatic or aromatic carboxyl, thiol, acyclic sulfide, cyclic disulfide, hydroxamic acid and trichlorosilane groups. The at least another functional group of said multifunctional organic molecules that binds chemicals may be a metal-binding and metal-detecting group selected from radicals derived from hydroxamic acids, bipyridyl, imidazol and hydroxyquinoline that can detect a metal ion such as $Cu^{2+}$, $Fe^{2+}$ and $Ru^{2+}$ metal ions. The at least another functional group of said multifunctional organic molecules that absorbs light is selected from aliphatic or aromatic hydroxamates, substituted aromatic groups such as cyanobenzoyl and methoxybenzoyl, bipyridyl groups, hydroxyquinoline groups, or imidazolyl groups to which a metal porphyrin or a metalophthalocyanin residue is attached. Examples of said multifunctional organic molecules are 2,3-di(p-cyanobenzoyl) tartaric acid (DCDC), 4,5-di(p-cyano-benzoyloxy)-1, 2-dithiane (DCDS), 4,5-di(p-methoxy-benzoyloxy)-1,2-dithiane (DMDS) and 1,2-dithiane-4,5-di (hydroxyquinoline) and the $Cu^{2+}$ complex thereof.

The device described in WO 98/19151 serves as a generic amplifier for chemical processes occurring on its surface. In one example, the device is based on a GaAs/(Al,Ga)As structure which is built in such a way that the current through it is extremely sensitive to the electric potential on its surface. As a result the device is very sensitive to any change in the charge distribution in molecules that are adsorbed on its surface (Gartsman et al., 1998; Vilan et al., 1998).

SUMMARY OF THE INVENTION

It has now been found, according to the present invention, that a device such as that described in WO 98/19151 can serve as a DNA sensor and can specifically be applied for DNA analysis and as a detector for DNA mutations. This device will be sometimes herein referred to as MOCSER.

The present invention thus relates to a semiconductor device (MOCSER) for the detection of a target DNA or RNA, said device being composed of:

(i) at least one layer of a conducting semiconductor;

(ii) at least one insulating or semi-insulating layer;

(iii) at least one single-stranded DNA probe directly adsorbed on the surface of an upper layer which is either a conducting semiconductor layer (i) or an insulating or semi-insulating layer (ii); and (iv) two conducting pads on the upper layer making electrical contact with the conducting semiconductor layer (i), such that electrical current can flow between them at a finite distance from the surface of the device.

In one embodiment, the semiconductor device of the invention is composed of one or more insulating or semi-insulating layers (1), one conducting semiconductor layer (2), two conducting pads (3), and a layer of at least one single-stranded DNA probe (4), characterized in that:

said conducting semiconductor layer (2) is on top of one of said insulating or semi-insulating layers (1), said two conducting pads (3) are on both sides on top of an upper layer which is either said conducting semiconductor layer (2) or another of said insulating or semi-insulating layers (1), making electrical contact with said conducting semiconductor layer (2), and said at least one single-stranded DNA probe (4) is adsorbed on the surface of said upper layer, between the two conducting pads (3).

In another aspect, the upper layer of the MOCSER has no DNA probe and at least one DNA probe can be adsorbed thereon at will by the user.

Thus, according to this aspect, the invention provides a semiconductor device (MOCSER) for the detection of a target DNA or RNA, said device being composed of:

(i) at least one layer of a conducting semiconductor;

(ii) at least one insulating or semi-insulating layer;

(iii) an upper layer which is either a conducting semiconductor layer (i) or an insulating or semi-insulating layer (ii) on the surface of which upper layer can be directly adsorbed at least one single-stranded DNA probe; and (iv) two conducting pads on the upper layer making electrical contact with the conducting semiconductor layer (i), such that electrical current can flow between them at a finite distance from the surface of the device.

In one embodiment of this aspect, the MOCSER is composed of one or more insulating or semi-insulating layers (1), one conducting semiconductor layer (2), and two conducting pads (3), characterized in that:

said conducting semiconductor layer (2) is on top of one of said insulating or semi-insulating layers (1), said two conducting pads (3) are on both sides on top of an upper layer which is either said conducting semiconductor layer (2) or another of said insulating or semi-insulating layers (1), making electrical contact with said conducting semiconductor layer (2), and whereby on the surface of said upper layer, between the two conducting pads (3), may be directly adsorbed a layer of at least one single-stranded DNA probe (4).

The semiconductor of layer (2) of a MOCSER of the invention may be a semiconductor selected from a III–V and a II–VI material, or mixtures thereof, wherein III, V, II and VI denote the Periodic Table elements III=Ga, In; V=As, P; II=Cd, Zn; VI=S, Se, Te. In preferred embodiments, the conducting semiconductor layer (2) is doped n-GaAs or doped n-(Al,Ga)As, preferably doped with Si.

In another embodiment, the one or more insulating or semi-insulating layers (1) of a device of the invention, that may serve as the base for the device, is a dielectric material selected from silicon oxide, silicon nitride or from an undoped semiconductor selected from a III–v and a II–VI material, or mixtures thereof, wherein m, V, II and VI denote the Periodic Table elements III=Ga, In; V=As, P; II=Cd, Zn; VI=S, Se, Te, and is preferably undoped GaAs or (Al,Ga)As substrate.

In one preferred embodiment, the MOCSER of the invention is based on a GaAs/(Al,Ga)As structure.

According to this preferred embodiment, there is provided a MOCSER wherein said conducting semiconductor layer (2) of doped n-GaAs is on top of a semi-insulating layer (1) of (Al,Ga)As which is on top of another semi-insulating layer (1) of GaAs, and on top of said conducting semiconductor doped n-GaAs layer (2) there is a semi-insulating undoped GaAs layer (1) to which is attached said layer of said at least one single-stranded DNA (4) probe.

According to this same preferred embodiment, there is further provided a MOCSER wherein said conducting semiconductor layer (2) of doped n-(Al,Ga)As is on top of an insulating layer (1) of undoped GaAs which is on top of a semi-insulating layer (1) of GaAs, on top of said conducting semiconductor doped n-(Al,Ga)As layer (2) there is a semi-insulating undoped (Al,Ga)As layer (1) on top of which there is an upper undoped GaAs semi-insulating layer (1), and said layer of at least one single-stranded DNA probe (4) is attached to the upper undoped GaAs semi-insulating layer (1).

The single-stranded DNA probe will vary according to the purpose of the detection and the type of DNA or RNA to be detected. In one preferred embodiment, the probe comprises a sequence that is complementary to a sequence of a target DNA or RNA.

Many genetic diseases and disorders are caused by a single or a plurality of mutations in one gene. For example, mutations are known in genes responsible for genetic disorders like cystic fibrosis (CF), hemophilia, Tay-Sachs disease, Gaucher's disease, sickle cell anemia, etc., and over 50% of cancerous tumors in humans carry a mutation in the tumor suppressor p53 gene.

When it is intended according to the invention to detect such a mutation, i.e. the target DNA in a sample comprises a mutation of a gene responsible for a genetic disease or disorder, the single-stranded DNA probe will comprise a sequence complementary to said mutation sequence. When two or more different mutations are known in the same gene or in separate genes, the device may contain two or more single-stranded DNA probes, each of said probes comprising a sequence being complementary to a different mutation sequence of said gene or genes responsible for a genetic disease or disorder.

The invention also relates to an array of semiconductor devices (MOCSERs) as described above, wherein each device in the array carries a different DNA probe.

In one preferred embodiment, at least one of said MOCSERs in the array carries a DNA probe comprising a sequence complementary to a sequence of a target DNA or RNA.

For the detection of a mutation in a target gene responsible for a disease or disorder, at least one of the devices in the array carries a DNA probe comprising a sequence complementary to said mutation sequence and at least another of said devices in the array carries a control DNA probe comprising a sequence complementary to the sequence of the normal gene corresponding to said mutation.

If there are two or more known mutations, the array will comprise as many devices comprising DNA probes complementary to the mutations and as many devices with control DNA probes complementary to the corresponding sequences of the normal gene.

The array of MOCSERs can also be used as an alternative to DNA chips for gene expression analysis, for example, for analysis of DNA or RNA expression in tissues or in any other expression system The invention further comprises a method for the detection of a target DNA or RNA which comprises:

(i) exposing the single-stranded DNA probe of at least one semiconductor device or of an array of the invention, to a sample containing the target DNA or RNA, under hybridization conditions; and (iii) monitoring either the current change resulting from the hybridization process when a constant electric potential is applied between the two conducting pads or measuring the change in the electric potential required to keep a constant current The DNA probe used in the present invention will be of a suitable length as usually used in DNA technology. Preferably, the probe is an oligonucleotide of above 10 nucleotides. For the detection of mutations, best results can be expected with 10–20 mer oligonucleotides. For DNA analysis, larger oligonucleotides may be suitable.

For the detection of a single mutation, a sample comprising a target DNA comprising said mutation will be reacted with a single-stranded DNA probe of a MOCSER of the invention comprising a sequence complementary to said mutation sequence. For the detection of multiple mutations, multiple complementary DNA probes may be adsorbed on the upper layer of a single MOCSER or an array of MOCSERs, each with a different complementary DNA probe, may be used.

The hybridization procedure is carried out by standard procedures well known in the art. A successful hybridization between the two complementary DNA strands is followed by a change in the current, when a constant electric potential is applied between the two conducting pads, or by a change in the electric potential required to keep a constant current.

For example, for the detection of cystic fibrosis (CF), an array of MOCSER units carrying DNA probes with sequences complementary to the prevalent CF mutations can be hybridized with target DNA samples obtained from different individuals. A comparison of the signals received from the array of MOCSER units carrying the CF specific probes annealed with the DNA of the tested samples may not only indicate that the tested DNA carries a CF mutation but may also identify the exact CF mutation within the DNA sample. Thus, the MOCSER technology can be an advantageous alternative to replace more cumbersome and expensive procedures used currently for detection of DNA mutations.

The MOCSER technology according to the invention can be used also for gene expression analysis as an alternative to DNA chips, avoiding the need to use labeled DNA. Thus, for example, to analyze the expression of a known gene in a tissue or in any expression system, e.g. bacteria, yeast, mammalian cells, plant cells, etc., RNA samples can be hybridized with an array of MOCSER units carrying DNA probes complementary to the sequences of the target gene.

Another application of the MOCSER technology consists in the analysis of non-identified DNA sequences such as ESTs. Thus, MOCSER units carrying DNA probes complementary to the sequences of known and unknown genes, for example of genes specifically expressed in particular tissues, are exposed to samples containing an unidentified denatured DNA sequence under hybridization conditions. The hybridization to a known DNA probe of a MOCSER unit is a tool for the characterization of the unidentified DNA, for example, for identification of the tissue of origin.

Other applications of DNA detection and analysis can be performed with the devices and methods of the invention and they are all encompassed herein within the scope of the invention.

BRIEF DESCRIPTION OF THE DRAWINGS

The present invention will be understood and appreciated more fully from the following detailed description, taken in conjunction with the examples and drawings, in which.

DETAILED DESCRIPTION OF THE INVENTION

Figure 1A:
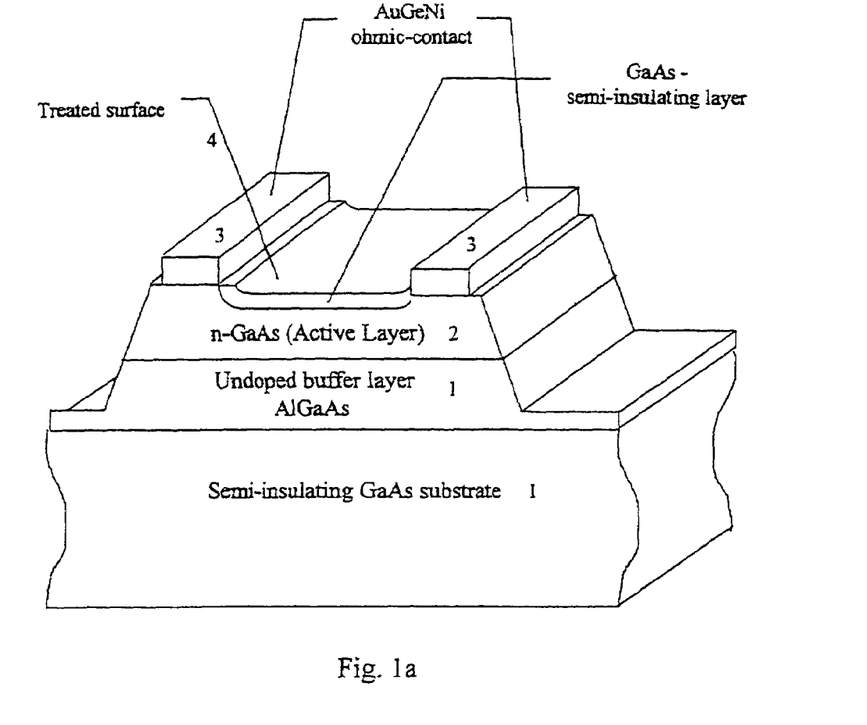
FIGS. 1a–1b depict schemes of the MOCSER device of the present invention: 1a—the layer structure; 1b—the layout.

A Molecular Controlled Semiconductor Resistor (MOCSER) according to the invention was developed as disclosed in WO 98/19151 as a multilayered GaAs based device as depicted in FIG. 1, which contains a n-doped GaAs upper layer (active layer, 50 nm thick) that is close to the surface. The active layer lies between semi-insulating layers, e.g. an undoped GaAs layer (about 5 nm thick) and a semi-insulating AlGaAs layer (about 150 nm thick) above a GaAs semi-insulating substrate, connected to two ohmic contacts, e.g AuGeNi.

In the MOCSER device, as disclosed before (Gartsman et al., 1998), the maximum electron density is at a depth of 30–50 nm from the surface in the active layer. Therefore, small changes on the surface, which change the surface potential, affect the resistance of the device. The MOCSER is very sensitive to chemical changes on the surface, but light, temperature, etc also affect it. Therefore, in order to make it a reliable sensor, the changes in the measured current that result from chemical process should be distinguished from the other effects.

The difference between the MOCSER and a common Si-FET (Field Effect Transistor) device is that in the latter the resistivity is sensitive to external field that can be applied by the gate, while in the MOCSER the adsorbed molecules modify the internal field (Vilan et al., 1998).

According to the present invention, a device for detection of irregularities in a DNA sequence is provided that is based on a MOCSER structure, preferably of a GaAs/(AlGa)As device, where on top of one of its surfaces a single-stranded DNA sequence is adsorbed. A current flows through the device when a voltage is applied between its two electrodes. When the adsorbed single-stranded DNA interacts with its complementary DNA sequence, the charge distribution in the molecules changes. The change in the charge distribution affects the current flowing through the device. Therefore specific binding can be detected and the kinetics of the reaction of the adsorbed molecule with its complementary one can be monitored.

The present invention will be more fully appreciated from the following detailed description and Examples taken in conjunction with the drawings.

Reference is now made to FIG. 1 which depicts schematically a DNA detector according to the invention based on a field effect transistor (FET) in which two electrodes are used. This FET-like device structure has an extra semi-insulating/undoped buffer (Al,Ga)As layer (1) (150 nm thick) on top of a semi-insulating GaAs substrate (1), a thin layer (50 nm thick) of conducting semiconductor n-GaAs (2) (active layer) on top of the semi-insulating (Al,Ga)As layer (1), a protective upper thin layer of undoped semi-insulating GaAs layer (1) (5 nm thick) covering the conducting semiconductor n-GaAs layer (2), and a thin film (4) of single-stranded DNA adsorbed on the undoped GaAs surface (1). Two conducting AuGeNi electrodes (3) serve as electrical contacts. These are the two ohmic contacts—source and drain, connected to the n-doped GaAs active layer that lies between the semi-insulating layers.

This molecular controlled semiconductor resistor (MOCSER) is highly sensitive to chemical changes on its surface. The molecules which are adsorbed on the GaAs surface change the surface potential, which affects the resistance of the MOCSER. The MOCSER also has a short response-time (Vilan et al., 1998) and its operation is very simple.

The detection of a specific sequence of DNA is important for diagnosis of diseases due to genetic defects, namely, changes in the naturally-occurring DNA sequence.

The hybridization reaction between complementary strands of DNA is a very important tool for the detection of DNA sequences. The combination of the sensitivity of the MOCSER with the recognition properties of DNA are the basic principles behind the present invention. The development of a DNA detector which is sensitive to hybridization reaction between complementary strands is achieved by the present invention by adsorbing a single strand of DNA on the MOCSER, which ssDNA will react with its complementary DNA strand present in a sample. Since this reaction will induce changes in the current through the MOCSER, a small electric potential applied between the two electrodes that have contact with the conducting layer in the device, will measure the change in the current. The changes in the current should be specific to the hybridization reaction, and should be different from the changes in the current due to other reactions. The change in the current indicates that the adsorbed single-stranded DNA is bound to its complementary strand. The rate of current change is directly correlated to the rate of the reaction between the molecules.

The invention will be further illustrated by the following non-limitative examples.

EXAMPLES a) General method

The electronic properties of semiconductor devices are strongly affected by the properties of the surface, which can be modified by adsorbed molecules. The interaction between the adsorbate and the substrate causes electrons to be transferred from the adsorbate to the substrate, or vice versa, depending on the position of the energy states in the two phases. Thus, the surface charge density and distribution can be changed by the adsorbates, and the effect of the adsorption can be determined.

GaAs is a III–V compound semiconductor with a direct band-gap of 1.42V. In the experiments herein, GaAs (100) surface was used and the single-stranded (ss)DNA was adsorbed on the GaAs surface. It is important to note that there are no reports in the literature of binding of DNA to GaAs. By characterizing the adsorption process and other reactions on the GaAs surface, the effect of DNA on the MOCSER can be understood better.

Employing a MOCSER surface made of GaAs(100), the adsorption of DNA on GaAs wafer serves as a model for the adsorption on the MOCSER. The ssDNA is deposited from a drop of its water solution on the GaAs wafer. The ssDNA is either unmodified or modified with a functional group such as carboxyl, thiol or sulfide at one end of the strand, in which case these groups bind chemically to GaAs.

The adsorption process is monitored using Fourier Transform Infra Red-spectroscopy (FTIR) spectroscopy and contact-angle measurements. By FTIR one can characterize the nature and the orientation of the adsorbed molecules on the GaAs surface. The ss DNA, e.g. an oligonucleotide, has several vibrational bands that can be detected by IR spectroscopy. The main features are: (1) carbonyl groups from different regions in the DNA bases: (2) C=C and C=N bonds from the conjugated rings of the bases: (3) aliphatic group of the sugar; and (4) phosphate group.

Contact-angle measurements can be used to study the packing of the adsorbed DNA molecules on the GaAs surface.

The reaction of the ssDNA with the complementary DNA stand is monitored via changes in the current through the MOCSER. A drop of the complementary DNA strand solution is deposited, followed by annealing, to allow the strands to bind through the complementary base-pairs. This reaction takes place both on the GaAs wafer and on the MOCSER. The change in the current through the MOCSER should be reproducible and specific to the hybridization reaction.

The current-voltage (I–V) characteristic of the MOCSER shows the change of the surface potential, resulting from the adsorbed DNA molecules. The chemical changes on the MOCSER surface affect its resistance and hence the current. The changes of the current in time are monitored at constant voltage values.

The selectivity of the reaction is determined by using mismatched, non-complementary DNA strands. Thus, the magnitude and the time constant of the change in the current through the MOCSER during the mismatched reaction should be different from the changes in the current during the hybridization reaction with the matched DNA strand.

b) The DNA solutions

The DNA which was adsorbed on the GaAs wafer was chemically synthesized and then purified (at the oligonucleotides synthesis laboratory at the Weizmann Institute of Science, Rehovot, Israel) in order to have almost 100% of the required sequence. For the studies with the XPS (X-ray Photoelectron Spectroscopy) and with the MOCSER, the DNA was not purified, and it was estimated to contain about 50% of the specified strand. The other strands in the mixture solution were shorter.

The oligonucleotides were dissolved in water (HPLC, after autoclave) to obtain solutions of 13 mM. The sequences of the adsorbed ssDNA used were either an oligonucleotide with a sequence of the gene responsible for the genetic disease cystic fibrosis (CF), herein identified as CF-normal (33 bases), or a shorter control oligonucleotide, herein control-B2 (20 bases), of the sequences:

CF-normal: 5'-ACCATTAAAGAAAATATCATCTTTG-GTGTTTCC-3'

Control B2: 5'-GTCAAGATGCTACCGTTCAG-3'

The CF-complementary and CF-non-complementary strands that were used were:

CF-complementary:
3—TGGTAATTTCTTTTATAGTAGAAACCA-CAAAGG-5'

CF-non-complementary (F-508):
5'-GGAAACACCAATGATATTTTCTTTAATGGT-3'

Control B2-complementary: 3'-CAGTTCTACGATG-GCAAGTC-5'

Control B2-non-complementary (3 bases different):
5'—CTGAATTATAGCATCTTGAC-3'

Control B2-non-complementary: 5'-CTGAATTATAG-CATCTTGAC-3'

The complementary or non-complementary stands were dissolved in a hybridization solution of: 1M NaCl, 10 mM Tris pH 7.6 and 0.005% Triton X-100, prepared according to the providers' instructions (Affymetrix, Gene Chip, Ye6100).

The adsorbed dsDNA was prepared as follows: equal amounts of the ssDNA and its complementary strand were mixed. The mixture was heated in a hot water bath of 70° C. for 10 min to assist the separation of the strands. Slow cooling to 35° C., in about 80–90 min, enabled the hybridization between the complementary strands. The cooled solution was concentrated to 1.3 mM.

c) Adsorption on GaAs Wafer

The samples of 4×4 mm$^2$ undoped-GaAs(100) (Am. Xtal Tech.) were boiled for 10 min in each of the following materials: trichloroethylene (chemically pure), acetone (analytical) and methanol (absolute).

The etching was performed according to the bromine/methanol procedure: each sample was actively rinsed through a multistep cycle, starting with a 0.05% v $Br_2$/methanol solution (bromine extra pure in absolute methanol) for 15 sec. Next, the sample was rinsed in absolute methanol and in water for 7–8 seconds each, followed by 15 sec rinsing in 1M KOH. The cycle was completed by rinsing in water and in methanol, and finally in the $Br_2$/methanol solution. This cycle was repeated three times and then it was rinsed in absolute methanol for 8 seconds more, followed by drying under nitrogen.

The clean and etched samples were put in open dry vials that were laid in a petri dish filled with water. The dishes with the samples were placed in an oven, at 23–28° C., in nitrogen atmosphere. The DNA was deposited on the sample from a 15 μL drop of the solution. After the introduction of DNA solution, the oven's door was closed and the nitrogen flow was stopped, for an overnight adsorption.

d) The Hybridization Process

The GaAs samples with the adsorbed ssDNA were laid in the same system as in the ssDNA adsorption procedure. The temperature of the oven was 55–60° C. The complementary/ non-complementary strand in the hybridization solution was heated in a hot water bath of 95–100° C. for 5 min, to induce denaturation of the DNA. The hybridization process was performed by depositing a 15 µl drop of the complementary/non-complementary strand solution on the sample for ~70 min.

After the hybridization, the samples were rinsed for 90 sec in a washing solution of 3 ml X20 SSPE, 5 µl 10% Triton X-100 and 7 ml water, prepared according to the providers' instructions (Affymetrix, Gene Chip, Ye6100) but with a concentration 6 times higher.

e) Infra-Red Measurements

Infrared (IR) spectroscopy probes the vibrational mode in molecules. This method can serve to characterize adsorbed molecules on surfaces, their chemical state and orientation. The spectrum is plotted as intensity vs. energy (in wavenumber units). Specific vibration in a certain chemical bond absorbs specific energy and has well characterized feature in the spectrum. Therefore, changes in the bonds or in their environment can be recognized by changes in the intensity or as shifts in the absorption energy in the spectrum.

Some of the advantages in studying DNA with IR, compared to other techniques, are: the possibility to test samples in various physical states (solutions, solids etc.), the possibility to study molecules that are different in size, and the high sensitivity that enable to investigate small amount of material.

The spectral range studied is 180°–800 $cm^{-1}$ and it consists of bands of different groups: the bases, the sugar and phosphate. Different conformation (A, B or Z) of DNA and the transition between them as the result of varied conditions can be determined. For example, when the relative humidity (R.H.) is decreased, the conformation changes from B (100% RH) to A (58% RH) as indicates by the changes in the spectral range of 1000–800 $cm^{-1}$. By analyzing the changes in the characteristic bands, the group that is bound to the surface can also be determined.

GaAs was used by Vilan et al, 1998, as a substrate for the adsorption of di-carboxilic derivatives through the carboxylic groups. The adsorption is indicated by the changes in the bands of these groups.

The results were compared with a reference spectrum. The reference was obtained from a GaAs sample after cleaning and etching, as described above. The adsorbed samples were measured after washing for 30 sec in ethanol, followed by 10 sec rinsing in acetone and drying with nitrogen. This measurement resulted in the spectrum indicating an excess of DNA on the surface. Next, the sample was rinsed for 90 sec in water and dried under nitrogen, to remove the excess of DNA.

The samples after the hybridization process were measured as follows: first measurement was taken after drying with nitrogen (excess spectrum), followed by measurement after rinsing the sample in a washing solution, as described in (c) above.

f) Experiments with the MOCSER

Figure 1B:
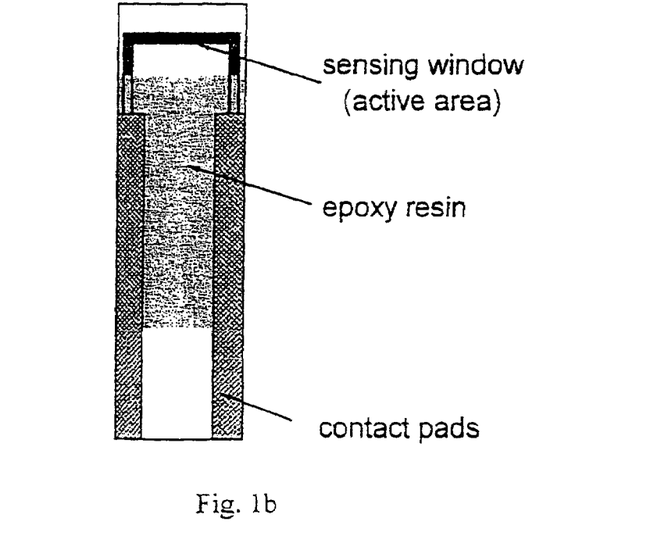

The MOCSER that is used for solution reactions has a needle-shape. The contact between the solution and the electric contacts is avoided by encapsulating material. Epoxy resin (FIG. 1b) was used in this work for the encapsulation.

Before the adsorption of DNA the surface of the MOCSER was etched. The etching process was performed by rinsing of the MOCSER in a 1:10 v/v $NH_4OH$:water solution for 3 sec, followed by rinsing in water for 10 sec and drying with nitrogen.

The etched MOCSER was put in the sample holder and in a vial with nitrogen. The vial was deposited in a desicator that was covered with a foil, to decrease the light effect on the MOCSER. The DNA was deposited from a 1–2 µl drop of the solution.

The adsorption on the MOCSER was monitored by 236-source-measure-unit of Keithley, USA. The potential between the source and the drain was set to 100 mV, and the current was measured as a function of time.

The hybridization process on the MOCSER was performed on the adsorbed sample while it is in the vial with nitrogen. The vial with the sample was put in an oven at ~80° C. The complementary/non-complementary strands were added from a drop of 1–2 µl solution of the DNA in water. The hybridization was performed for ~100 min, while simultaneously the current through the MOCSER was monitored.

Example 1

Adsorption of ssDNA on GaAs Surface

IR spectroscopy was used to investigate the adsorption of DNA on the GaAs surface and to examine the reactivity of the adsorbed DNA. First, the binding group was determined. Second, the hybridization process of the adsorbed DNA was characterized. The adsorbed DNA strands were either of the CF sequence (33 bases) or Control B2 sequence (20 bases), as described in section (b) above.

Figure 2A:
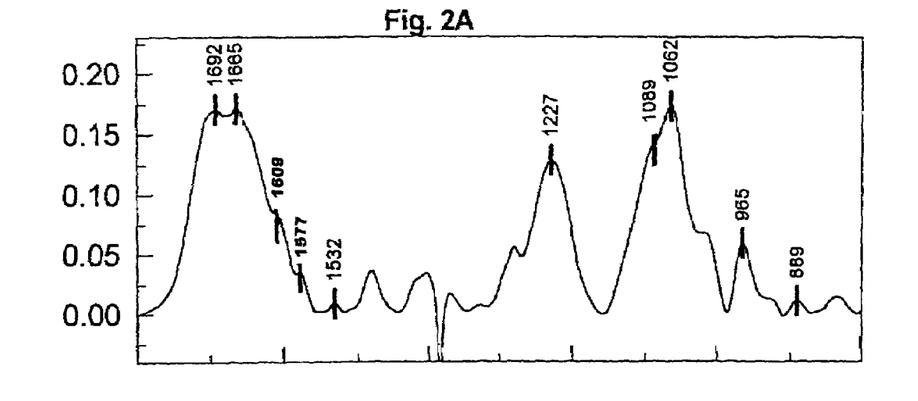
FIGS. 2A–C show infra red (IR) spectra of ssDNA: free DNA (cystic fibrosis (CF) 33-mer peptide) in KBr pellet (A); DNA (control B2) on GaAs, after washing with ethanol (B) and after rinsing in water (C).
Figure 2B:
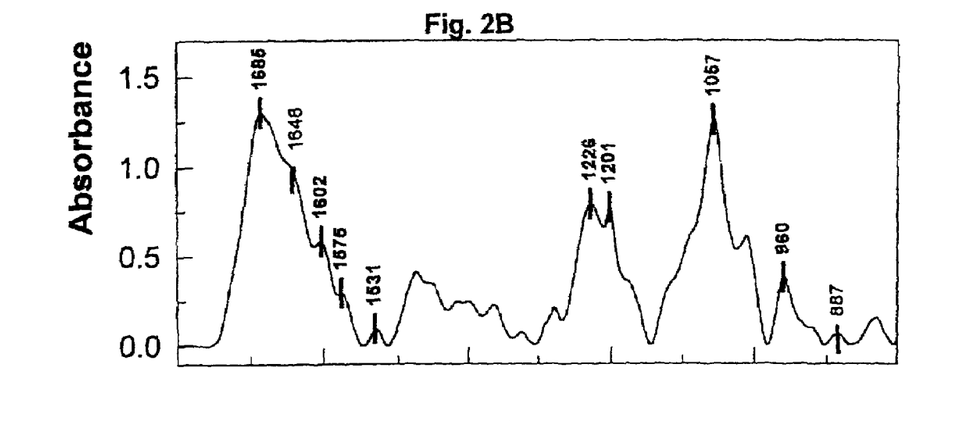
Figure 2C:
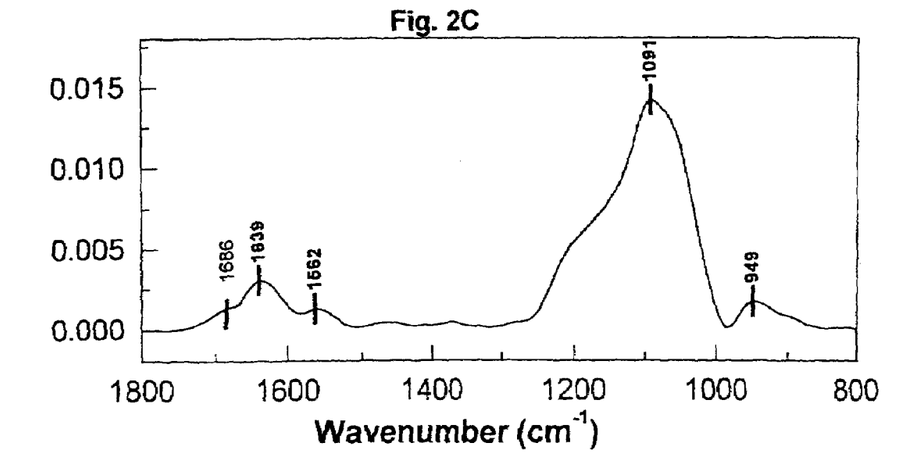

FIG. 2 shows the IR spectra of free DNA (FIG. 2A) and of the adsorbed ssDNA on GaAs (FIGS. 2B,C). The free DNA was measured as a KBr pellet of dry ssDNA (CF sequence, mixed with hexane). The adsorbed ssDNA was obtained from depositing a drop of DNA (Control B2) on a GaAs sample, as described in the Experimental section. The reference was a clean etched GaAs sample. The 'excess' spectrum (FIG. 2B) was taken after washing the adsorbed sample with ethanol. As a result of the washing, white solid was precipitated on the surface of some of the samples, and other samples had a dark covering layer. The 'rinsing' spectrum (FIG. 2C) was taken after rinsing the sample with water. Most of the visible cover material was removed and the surface was clear.

To determine the group that binds the DNA to the surface, the bands in the spectra are assigned (Table 1) and the shifts in the main bands of the bases and of the phosphate can be analyzed from the changes in the bands position.

In general, the spectrum of the free DNA (FIG. 2A) is similar to the spectrum of crystalline DNA, as was obtained by Urpi et al., Nuc. Acid Res., 17:6669 (1989). The 'excess' spectrum (FIG. 2B) is similar to the spectrum of free DNA. However, the spectrum after rinsing (FIG. 2C) is different from the two above.

The bands that are assigned to the bases of the DNA include the amide carbonyl band at ~1690–1660 $cm^{-1}$, and the bands at 1650–1530 $cm^{-1}$ of the amide and of the double bonds in the bases ring. In this spectral range, the peaks in the 'excess' spectrum are similar in shape and position to those of the free DNA. However, in the excess spectrum the peak at 1665 $cm^{-1}$ of the free DNA is reduced and a new peak appears at 1648 $cm^{-1}$. After rinsing, the relative intensity of this spectral range is reduced compared to the phosphate range. Within the bases spectral region, the relative intensity of the peaks is changed, but the positions are almost the same as in the excess spectrum. The peak in 1685 $cm^{-1}$ is shifted to 1686 $cm^{-1}$ and the peak at 1648 $cm^{-1}$ is shifted to 1639 $cm^{-1}$. However, their relative intensity is reversed. The peak at 1602 cm$^{-1}$ is not seen in the 'adsorbed DNA' spectrum and it is probably a part of the broad band at 1639 cm$^{-1}$. The peaks that were at 1575 cm$^{-1}$ and at 1531 cm$^{-1}$ are merged to one peak at 1562 cm$^{-1}$ in the rinsing spectrum.

TABLE 1

The assignments of the IR bands (FIGS. 2A–C) to the DNA groups

| Peaks position of SsDNA in KBr pellet (free DNA) (cm$^{-1}$) | Assignment | Peaks position of ssDNA after ethanol washing (excess) (cm$^{-1}$) | Peaks position of ssDNA after rinsing (adsorbed DNA) (cm$^{-1}$) |
|---|---|---|---|
| 1692, 1665 | C=O stretch in amide (Amide I) | 1685 | 1686 |
| 1609, 1577, 1532 | 1. Double bonds (C=C, C=N) in the bases plane. 2. N—H bend in amide (Amide II) | 1648 1602, 1575, 1531 | 1639 1562 |
| 1227 | Phosphate antisymmetric stretching | 1226, 1201 | No separated peak |
| 1089 1062 | Phosphate symmetric stretching | 1089 1057 | 1091 |
| 965 | C—C, P—O | 960 | 949 |
| 889 | Sugar-phosphate | 887 | No peak |

The bands at the spectral range of ~1230–800 cm$^{-1}$ are assigned to the phosphate and sugar-phosphate vibrations at the backbone of the DNA. This spectral range in the 'excess' spectrum looks similar to the free DNA spectrum Two separated areas are obtained: the range with a peak at ~1227 cm$^{-1}$ and the range with the peak at ~1062 cm$^{-1}$. The phosphate antisymmetric stretching at 1227 cm$^{-1}$ in the free DNA, is observed in the excess spectrum and additional peak is seen at 1201 cm$^{-1}$. The phosphate symmetric stretching at 1062 cm$^{-1}$ is slightly shifted to 1057 cm$^{-1}$. The intensity of the peak at 1089 cm$^{-1}$ is reduced, compared to the neighboring peaks.

After rinsing, the two areas of the phosphate bands are combined to a strong band with a peak at 1091 cm$^{-1}$. The band at 1226 cm$^{-1}$, is significantly shifted to lower frequencies and cannot be seen as separated peak now. The other area of the phosphate bands is shifted a little to the opposite direction. The peak at 960 cm$^{-1}$ is only slightly shifted to 949 cm$^{-1}$. The peak at 887 cm$^{-1}$ from the excess spectrum is probably included within this broad band.

Based on the changes in the spectrum of the adsorbed DNA, compared to the excess DNA spectrum, we can conclude that the adsorption of ssDNA on GaAs is indicated by major shifts in the phosphate bands. Minor shifts are observed in the bands that are assigned to the bases.

Example 2

Reactions of the Adsorbed DNA

Figure 3:
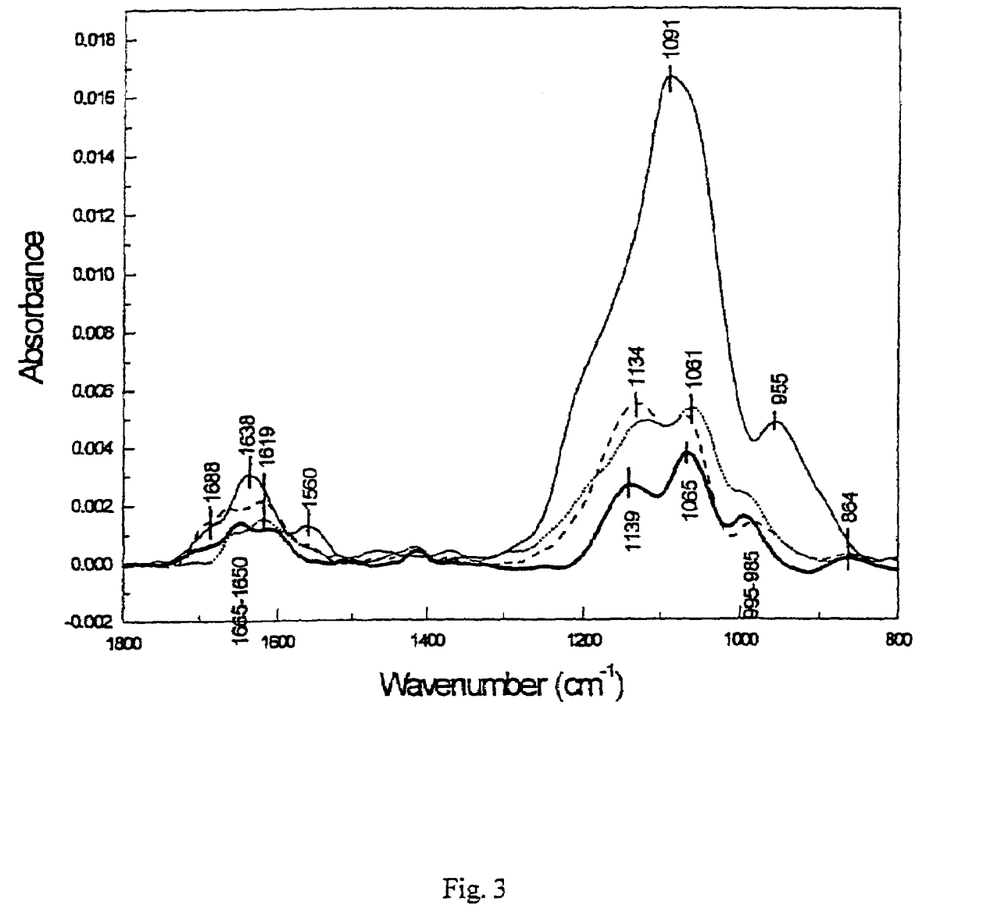
FIG. 3 depicts IR spectra of adsorbed ssDNA (control B2)—after rinsing (solid line), after hybridization with complementary strand (thick solid line), and after reaction with the same strand (dashed line) and with non-complementary strand of 3-bases modified (dotted line). The presented hybridization spectra are shown after the subtraction of the adsorbed ssDNA (rinsing) spectrum

FIG. 3 shows the IR spectra of the adsorbed ssDNA (solid line) after reactions with complementary (thick solid line) and with non-complementary (dashed and dotted lines) strands. The non-complementary strand is either the same sequence as the adsorbed strand or the same as the complementary sequence but modified by 3 bases.

Table 2 shows the positions of the main bands in the IR spectra, before and after the hybridization process.

The various spectra after the hybridization are different from each other in the relative intensities of the peaks. The intensity of the spectrum of complementary strand is slightly lowered, compared to the spectra of the non-complementary strands. However, the peaks positions appear at similar frequencies and only slightly shifted in energy from one another.

The bands that correspond to the bases, at the spectral range of ~1700–1550 cm$^{-1}$, are slightly changed followed the hybridization. The shoulder at 1688 cm$^{-1}$ in the spectrum of adsorbed ssDNA, is still observed after the hybridization. However, there are also new features in the range of 1665–1650 cm$^{-1}$ and at 1619 cm$^{-1}$, and the peak that is observed at 1638 cm$^{-1}$ in the adsorbed ssDNA is reduced after the hybridization.

TABLE 2

The assignments of IR spectral bands (FIG.3) to the DNA groups.

| Assignment | Peaks position of ssDNA after rinsing (adsorbed DNA) (cm$^{-1}$) | Peaks position of ssDNA after Hybridization with complementary and with non-complementary strands (cm$^{-1}$) |
|---|---|---|
| C=O strech in amide (Amide I) | 1688 | 1688 1665–1650 |
| 2. Double bonds (C=C, C=N) in the bases plane. | 1638 | 1619 |
| 2. N—H bend in amide (Amide II) | 1560 | 1560 |
| Phosphate antisym. Stretching | No separated peak | 1139–1134 |
| Phosphate sym. Stretching | 1091 | 1065–1061 |
| C—C, P—O | 955 | 995–985 |
| Sugar-phosphate | No peak | 864 |

The spectral range of the phosphate bands is changed followed the hybridization process. Instead of one broad band at 1090 cm$^{-1}$, as is seen in the spectrum of adsorbed ssDNA, two peaks are observed, at 1139–1134 cm$^{-1}$ and at 1065–1061 cm$^{-1}$. These bands, in the spectrum of the complementary strand, are slightly shifted to higher frequencies, relative to the non-complementary strands. The peak that is at 955 cm$^{-1}$, in the rinsing spectrum, is shifted to higher frequencies followed the hybridization.

Example 3

Adsorption of Double-Stranded DNA (dsDNA)

Figure 4:
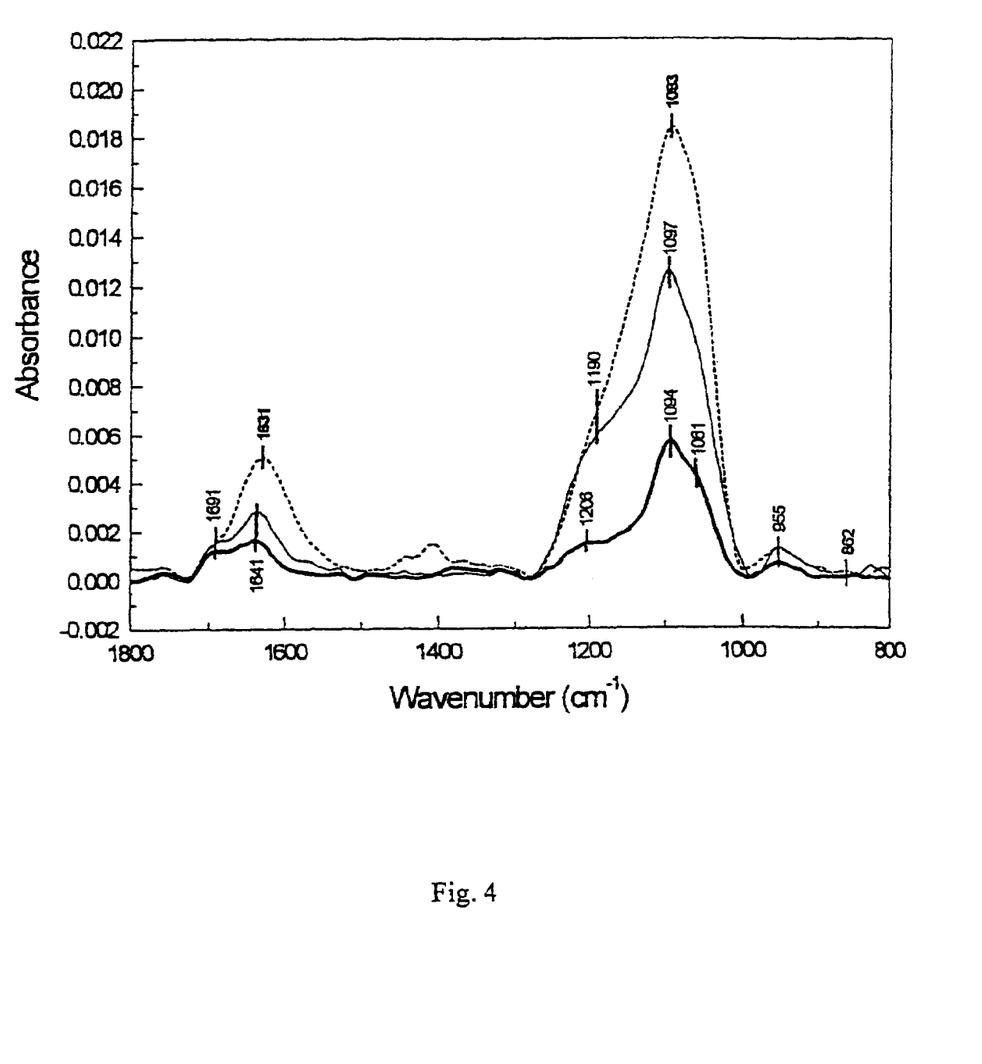
FIG. 4 depicts IR spectra of adsorbed dsDNA (control B2) (thick solid line), adsorbed ssDNA (solid line), and adsorbed ssDNA after hybridization with its complementary strand (dashed line)

FIG. 4 presents the IR spectrum of adsorbed dsDNA (thick solid line), which is compared to adsorbed ssDNA (solid line) and to the hybridization with complementary strand (dashed line). The dsDNA (control B2) was adsorbed on the GaAs samples in the same manner as the ssDNA.

TABLE 3

The assignments of IR spectral bands (FIG. 4) to the DNA groups

| Assignment | Peaks position of ssDNA, after rinsing (adsorbed DNA) (cm$^{-1}$) | Peaks position of dsDNA, after rinsing (adsorbed DNA) (cm$^{-1}$) | Peaks position of Hybridization with complementary strand (cm$^{-1}$) |
|---|---|---|---|
| C=O strech in amide (Amide I) | 1691 | 1691 | 1691 |
| 3. Double bonds (C=C, C=N) in the bases plane 2. N—H bend in amide (Amide II) | 1641 | 1641 | 1631 |
| Phosphate antisym. Stretching | 1190 | 1206 | 1091 |
| Phosphate sym. Stretching | 1097 | 1094 1061 | 1091 |
| C—C, P—O | 955 | 955 | 955 |
| Sugar-phosphate | No peak | 862 | 862 |

To determine that indeed the DNA is adsorbed through the phosphate, the spectrum of the dsDNA is compared to the spectrum of the adsorbed ssDNA. To further characterize the hybridization process, the spectrum of adsorbed ssDNA after the reaction with its complementary strand is compared to that of the adsorbed dsDNA. The bands in FIG. 4 are assigned in Table 3, above.

The features in the bases spectral range (~1700–1550 cm$^{-1}$) look similar in all the spectra. In the phosphate range, the antisymmetric stretching is observed in the dsDNA (1206 cm$^{-1}$) and is shifted from that of the ssDNA (1190 cm$^{-1}$). In the spectrum of the complementary strand, this peak is a part of the broad band that has a peak at 1093 cm$^{-1}$. The symmetric stretching in the dsDNA appears at 1094 cm$^{-1}$ and at 1061 cm$^{-1}$. In the spectra of the ssDNA and of the complementary strand, these bands appear at 1097 cm$^{-1}$ and at 1093 cm$^{-1}$, respectively.

The dsDNA and the ssDNA spectral features are almost identical. The spectrum of the complementary strand is in general similar to that of dsDNA.

Example 4

MOCSER Measurements

The effect of the adsorption of DNA on the current through the MOCSER was studied. After the adsorption of the ssDNA, the reactions with the complementary and with non-complementary strands were performed. The results are presented below. The CF sequence was used in these experiments.

4.1 Adsorption of ssDNA

Figure 5:
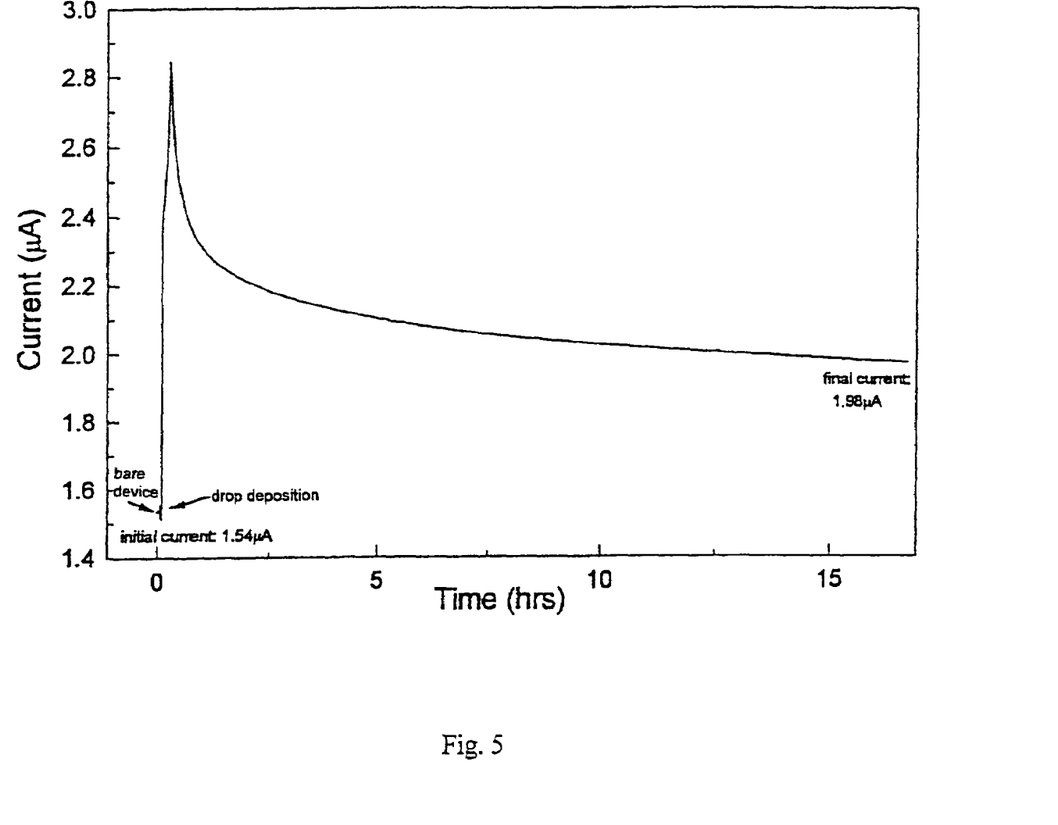
FIG. 5 shows the measured current through the MOCSER during the adsorption of ssDNA (CF sequence). A constant potential of 100 mV is kept between the source and the drain.

FIG. 5 shows the change in the current through the MOCSER following the adsorption of ssDNA. A drop of ssDNA was deposited on the etched MOCSER, and the current was recorded as a function of time.

The current through the bare device, before the adsorption, was 1.54 µA. Following the drop deposition the current increases, after ~15 min, to a value of ~2.85 µA. A slower decrease in the current to a value of 1.98 µA is observed after about 16 hrs. After rinsing the MOCSER in water for 90 sec, the current decreased to 1.88 µA (not shown in the graph).

Hence, the adsorption of ssDNA on the MOCSER is indicated by a net increase in the current through the MOCSER.

4.2 Reactions of the Adsorbed ssDNA

Figure 6A:
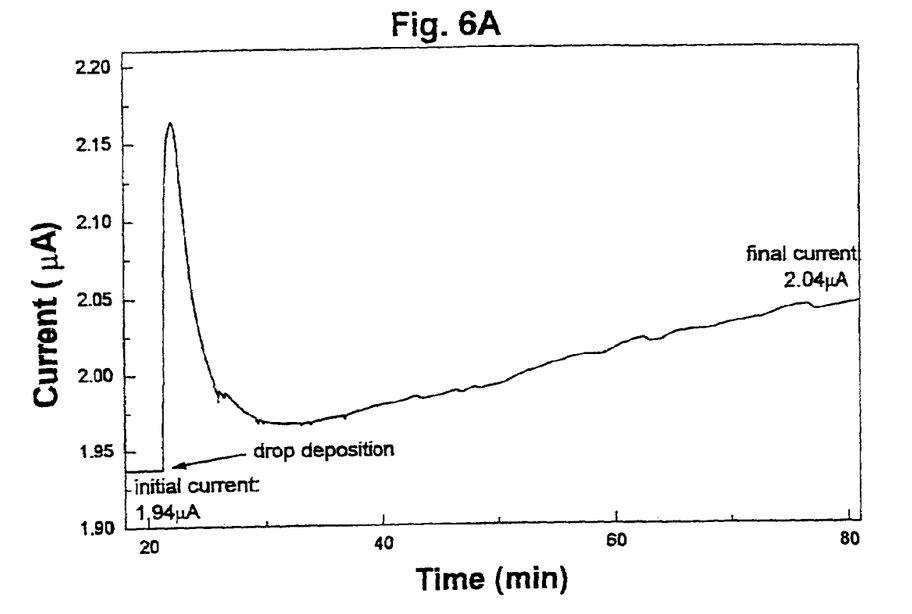
FIGS. 6A–6B show the measured current through the MOCSER, while an adsorbed ssDNA (CF sequence) reacts with its complementary strand (6A) and with a non-complementary strand (F-508) (6B).
Figure 6B:
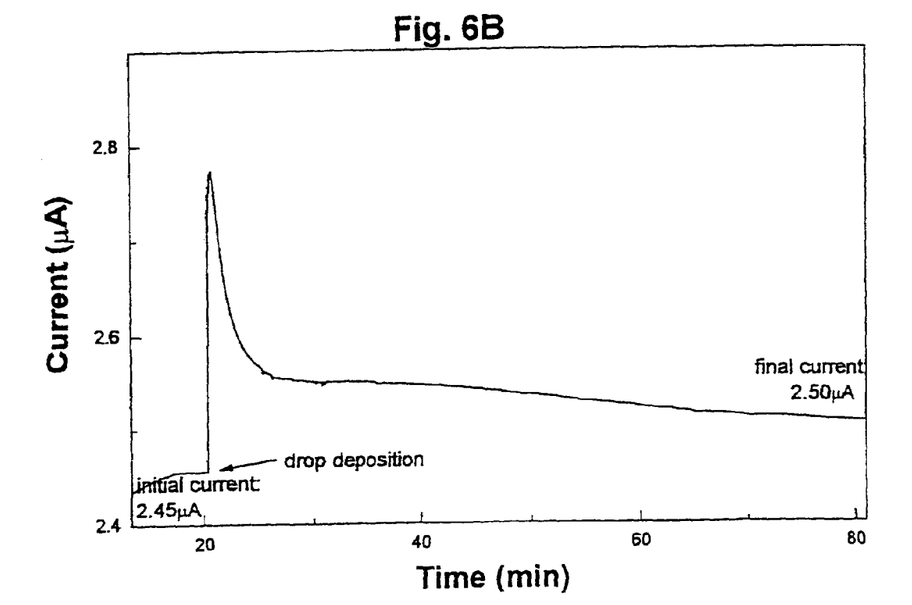

FIG. 6 shows the change in current through the MOCSER following the reactions of the adsorbed ssDNA. FIG. 6A shows the measured current during the hybridization with the complementary strand. FIG. 6B presents the measured current when the reaction with a non-complementary strand (F-508) was performed. Both reactions were measured for about 2 h, at 60–85° C.

The current through the bare devices, before the adsorption, was 1.94 µA and 2.45 µA for the devices used for obtaining the results shown in FIGS. 6A and 6B, respectively. Following the drop deposition, the current significantly increased in both devices. Then, the current was decreased until it reached its final value, after about 80 min. When a complementary strand was added the final current was 2.04 µA, and in the case of the non-complementary strand, it was 2.5 µA.

After cooling the devices, they were rinsed in water for 90 sec. As a result, the current decreased to 1.85 µA and to 1.82 µA, with the complementary and with non-complementary strand, respectively (not shown).

The net increase in the current of the MOCSER was higher for the device with the complementary strand, compared to that with non-complementary strand.

Example 5

X-ray Photoelectron Spectroscopy (XPS) Measurements

XPS measurements were performed in order to further characterize the adsorption of DNA on GaAs surface. The XPS data provides a quantitative chemical analysis, which can be used to calculate the thickness of the layer. In addition, it can point at the actual binding to the substrate, via the corresponding line shifts and depth profile information.

The ssDNA and the dsDNA (CF sequences) were adsorbed on n-GaAs samples, in the procedure that is used for adsorption on GaAs.

5.1 The thickness of the Adsorbed Layer

TABLE 4

Calculated thickness of the overlayer (in angstroms) of GaAs samples covered with ssdNA or with dsDNA.

| Method of calculation And the take off angle | ssDNA | dsDNA |
|---|---|---|
| 1. As, 90° | 12.1 | 8.19 |
| 1. As, grazing angle (35° for ssDNA, 30° for dsDNA) | 15.65 | 15.2 |
| 2. Ga, 90° | 19.5 | 14.1 |
| 2. Ga, grazing angle | 20.3 | 15.8 |
| 3. Coverage + substrate, 90° | | |
| assuming: $\lambda_1 = \lambda_2$ | 16.2 | 12.2 |
| corrected for: $\lambda_1 \neq \lambda_2$ | 15.5 | 11.6 |
| 3. Coverage + substrate, grazing angle | | |
| assuming: $\lambda_1 = \lambda_2$ | 17.4 | 12.3 |
| corrected for: $\lambda_1 \neq \lambda_2$ | 16.9 | 11.9 |

Based on the attenuation of the photoelectrons, the thickness of the adsorbed ssDNA and dsDNA can be calculated in three different methods. The first and the second one are based on the electrons ejected from the substrate only (from Ga and As). Taking advantage of the fact the electrons attenuation is dependent on its kinetic energy, comparison of different Ga or As lines can yield the overlayer thickness. The third method is based on the ratio between the overlayer and the substrate signals. The calculated thickness values from the various methods are presented in Table 4, above.

The average calculated thickness is: 12–20 Å and 8–16 Å for adsorbed ssDNA and dsDNA, respectively. The calculated thickness in grazing take off angle is larger than in the normal angle. Clearly, the thickness calculated based on the signal from Ga is larger than the value obtained based on the As peak. This indicates the existence of As oxides at the interface. However, the relative concentration of Ga is larger than As. This might originate from using wrong sensitivity factor during the data analysis, or from oxidized Ga on the surface. This may be due to the fact that the oxidized As is spectrally resolved, but not the oxidized Ga. The average thickness of the oxide layer is calculated to be ~5 Å (applying method-3 for the ratio between the oxide peak and the As peak). It seems that Ga oxides are considerably lower in intensity, hence, the electrons ejected from Ga "see" thicker coverage that contains both the adsorbed molecules and the oxides on the As (~5 Å). Therefore, we conclude that the thickness of the DNA is ~10–15 Å.

Example 6

MOCSER Arrays

The need to decipher the complexity of the genetic code and of gene expression for the purpose of drug design has dictated the need for a fast and efficient screen of a large number of DNA molecules. DNA screening is required for various applications, including a search of an unknown gene from a pool of known genes; identification of single-base mutations within a characterized gene, several thousand of bases long; or for the determination of the expression pattern of hundreds of genes in certain tissues. DNA arrays, also known as DNA chips, were developed as a tool to meet the technical challenge of such time-consuming screening applications. As such, DNA arrays appear to become the biotechnology tool of the next decade.

At the heart of the DNA chips technology lies a surface onto which the DNA samples to be screened are attached in an organized fashion, creating an array or a grid of spots. Each spot contains a different DNA sequence. In the technology used so far, the target or sample DNA, carrying a radioactive or a fluorescence label, is allowed to hybridize with the DNA attached to the array. The level of hybridization of the target DNA to the different spots of the array is detected by scanning the array and monitoring the level of labeling (radioactive, fluorescence, etc.) at each spot. The technical challenges presented by the technology of the DNA chips stem from the arrayed nature of the device: 1. Attaching a large number of different DNA sequences as discrete spots with high proximity onto a surface 2. The requirement for a perfect alignment between the detector grid and the array in order to achieve high-resolution detection of the hybridization signal within a closely spaced grid. These technical difficulties are the reason for the high cost of current commercially available DNA chips. In addition, the need to use a radioactive or a fluorescent DNA probe complicates both probe preparation and, more significantly, the analysis of the results due to a low signal to noise ratio.

The MOCSER technology provides an excellent and superior alternative to DNA chips in scanning a large number of DNA target molecules with a DNA probe. Due to the ability of the MOCSER to distinguish between single and double-stranded DNA by different electrical currents, each spot on a DNA array can be replaced by a MOCSER unit, containing one type of single-stranded DNA probe. The difficulty in fabricating the arrayed spots in a traditional DNA chip is therefore eliminated. Upon addition of a non-labeled single-stranded target DNA to each MOCSER unit, the level of hybridization of the target to each probe sequence within a MOCSER unit is detected electrically. Therefore, the need for high resolution and perfect alignment between the detector and the array is overcome. In addition, no labeling of the DNA probe is required.

Discussion

On the base of the IR spectra analyzing and the XPS data, the phosphate is suggested as the binding group of the DNA to the GaAs surface. The adsorption of DNA can be identified by the changes in the IR spectra. The excess DNA on the GaAs surface (FIG. 2B) has an IR spectrum that is similar to the free DNA (FIG. 2A). Both of the spectra are similar to the spectrum of crystalline DNA. The adsorption of DNA molecules through the backbone is indicated also by the adsorption of dsDNA. The IR spectrum of the adsorbed dsDNA has similar spectral features as the adsorbed ssDNA (FIG. 4). The binding of dsDNA to the surface is possible only through the backbone and not through the bases, which are bound by hydrogen bonds. Therefore, we conclude that similar backbone-substrate binding occurs in the ssDNA.

The XPS measurements give further support to the conclusion that the adsorption of DNA is through the phosphate.

According to the invention, we showed the binding of DNA directly to the GaAs surface without any modification. This is in contrast to previously developed DNA sensors, in which the probe DNA was adsorbed onto the surface through an additional binding group. On silicone surfaces, ssDNA is bound via a modified amino binding group, and on a gold surface DNA binding is done after modifying the adsorbed DNA with sulfides at the end.

When ssDNA is adsorbed on the MOCSER a net increase in the current through the MOCSER is observed (FIG. 2). A sharp increase in the measured current is followed immediately with the deposition of the DNA. This can be attributed to the solution, since we found that when we put a drop of pure water on the MOCSER, a sharp increase in the measured current is observed (the results are not shown in this work). In the case of DNA adsorption, a net increase in the current is obtained even after very long time. This final increase in the current is due to the change in the surface potential of the MOCSER by the adsorbed DNA. This change causes a reduction in the depletion of the active layer, and hence the resistance of the MOCSER decreases.

The selectivity of the hybridization process was studied both on the GaAs wafer and on the MOCSER.

Considering the changes in the intensity of the IR spectra (FIG. 3), the intensity of the spectrum with the complementary strand (thick solid line) is lowered, compared to the non-complementary strands (dashed and dotted lines). In particular, the intensity of the peaks is reduced for the bands of the bases at 1619 cm$^{-1}$ and 1560 cm$^{-1}$, and at the phosphate band at 1139 cm$^{-1}$. This can be explained by a stronger base-stacking interaction followed the hybridization process. Following the denaturation process (the separation of the dsDNA) the IR spectral bands of the bases and of the phosphate are increased. The results obtained after the adsorption of dsDNA (FIG. 4) provide further evidence to this conclusion. The intensity of the peaks of the bases and of the phosphate (especially, the peaks at 1641 cm$^{-1}$ and at 1206 cm$^{-1}$) are lowered, compared to those of ssDNA. The spectrum obtained after reaction of a complementary strand with an adsorbed ssDNA (FIG. 4, dashed line) has higher intensity at these bands, compared to the dsDNA (FIG. 4, solid line). Additional single-strands that adsorb on the surface can explain this. They are partially adsorbed as ssDNA and not all were hybridized. As a result, the intensities of peaks related to the bases and to the phosphate are increased, compared to the dsDNA spectrum.

The hybridization on the MOCSER resulted in a net increase in the measured current, both with the complementary and with the non-complementary strands. However, the current increased more following the reaction with the complementary strand.

The adsorbed DNA stabilizes the surface of the MOCSER, as can be observed in the measured current, which is stable and shows high signal to noise ratio. This is an advantage in terms of stabilizing the GaAs surface of the MOCSER.

After about 2 months from the adsorption of DNA, the MOCSERs that were kept in vacuum at room temperature, were still active (not shown). This result is important for the development of a sensor that can be active for long time.

The sensitivity of the MOCSER is high. When a 1.3 mM DNA solution was used, the change in the current was in the order of tenths of micro-amperes. The selectivity of the MOCSER in the preliminary results looks promising, as we obtained different changes in the current in the reaction with a complementary strand, compared to the non-complementary strand.

The adsorption of DNA onto a GaAs surface is the first step towards the development of a DNA sensor that is based on the MOCSER. In this work, DNA was bound directly onto the GaAs surface, through the phosphate groups, without using any modification of the surface or of the adsorbate. The chemistry of the adsorption onto the GaAs wafer was characterized. The electrical change in the MOCSER as a result of the adsorption on its surface was determined.

The selectively binding of the complementary strands during the hybridization process is used in DNA sequence detectors. Here, we could distinguish both with the GaAs wafer and with the MOCSER between the reaction of the adsorbed ssDNA with its complementary strand compared to the non-complementary strands.

REFERENCES

1. Gartsman K., Cahen D., Kadyshevitch A., Libman J., Moav T., Naaman R., Shanzer A., Umansky V. and Vilan A., "Molecular control of a GaAs transistor", *Chem. Phys. Lett.*, 283, 301 (1998).
2. Livache T., Fouque B., Teoule R., *Anal. Biochem.*, 217, 248 (1994).
3. Vilan A., Ussyshlkin V. R., Gartsman K., Cahen D., Naaman R, Shanzer A., "Real time monitoring of adsorption kinetics: Evidence for 2-site adsorption mechanism of dicarboxylic acids on GaAs(100)", *J. Phys. Chem*(B), 102, 3307–3309 (1998).
4. Wang J., Cai X., Rivas G., Shiraishi H., Farias P. A. M., Dontha N., *Anal. Chem.*, 68, 2629 (1996).

The invention claimed is:

1. A semiconductor device composed of one or more insulating or semi-insulating layers, one conducting semiconductor layer, two conducting pads, and a layer of at least one single-stranded DNA probe, wherein:

said conducting semiconductor layer is on top of one of said insulating or semi-insulating layers, said two conducting pads are on both sides on top of an upper layer which is either said conducting semiconductor layer or another of said insulating or semi-insulating layers, making electrical contact with said conducting semiconductor layer, and said layer of at least one single-stranded DNA probe is directly adsorbed on the surface of said upper layer, between the two conducting pads, wherein exposure of said single-stranded DNA probe to a sample containing a target DNA or RNA, under hybridization conditions, causes either a current change resulting from the hybridization process when a constant electric potential is applied between the two conducting pads or a change in the electric potential required to keep a constant current.

2. A semiconductor device according to claim 1, wherein said conducting semiconductor layer is a semiconductor selected from a III–V and a II–VI material, or mixtures thereof, wherein III, V, II and VI denote the Periodic Table elements III=Ga, In; V=As, P; II=Cd, Zn; VI=S, Se, Te.

3. A semiconductor device according to claim 1, wherein said conducting semiconductor layer is doped n-GaAs or doped n-(Al,Ga)As.

4. A semiconductor device according to claim 1, wherein the one or more insulating or semi-insulating layers, that may serve as the base for the device, is a dielectric material selected from the group consisting of silicon oxide, silicon nitride and an undoped semiconductor selected from a III–V and a II–VI material, or mixtures thereof, wherein III, V, II and VI denote the Periodic Table elements III=Ga, In; V=As, P; II=Cd, Zn; VI=S, Se, Te.

5. A semiconductor device according to claim 4, wherein said undoped semiconductor is undoped GaAs or undoped (Al,Ga)As.

6. A semiconductor device according to claim 3, wherein said conducting semiconductor layer is a layer of doped n-GaAs which is on top of a semi-insulating layer of (Al,Ga)As which is on top of another semi-insulating layer of GaAs, and on top of said conducting semiconductor doped n-GaAs layer there is a semi-insulating undoped GaAs layer to which is attached said layer of said at least one single-stranded DNA probe.

7. A semiconductor device according to claim 3, wherein said conducting semiconductor layer is a layer of doped n-(Al,Ga)As which is on top of an insulating layer of undoped GaAs which is on top of a semi-insulating layer of GaAs, on top of said conducting semiconductor doped n-(Al,Ga)As layer there is a semi-insulating undoped (Al,Ga)As layer on top of which there is an upper undoped GaAs semi-insulating layer, and said layer of at least one single-stranded DNA probe is attached to the upper undoped GaAs semi-insulating layer.

8. A semiconductor device according to claim 1, wherein said at least one single-stranded DNA probe comprises a sequence complementary to a sequence of a target DNA or RNA.

9. A semiconductor device according to claim 8, wherein said at least one single-stranded DNA probe comprises a sequence complementary to a mutation sequence of a gene responsible for a genetic disease or disorder.

10. A semiconductor device according to claim 9, comprising two or more single-stranded DNA probes each of said probes comprising a sequence being complementary to a mutation sequence of a gene responsible for a genetic disease or disorder.

11. An array of semiconductor devices according to claim 1, wherein each device in the array carries a different DNA probe.

12. An array of semiconductor devices according to claim 11, wherein at least one of said devices in the array carries a DNA probe comprising a sequence complementary to a sequence of a target DNA or RNA.

13. An array of semiconductor devices according to claim 12, wherein at least one of said devices in the array carries a DNA probe comprising a sequence complementary to a mutation sequence of a target gene responsible for a genetic disease or disorder and at least another of said devices in the array carries a control DNA probe comprising a sequence complementary to the sequence of the normal gene corresponding to said mutation.

14. A method for the detection of a target DNA or RNA which comprises:
   (i) exposing the single-stranded DNA probe of at least one semiconductor device according to claim 1 to a sample containing the target DNA or RNA, under hybridization conditions; and
   (ii) monitoring either the current change resulting from the hybridization process when a constant electric potential is applied between the two conducting pads or measuring the change in the electric potential required to keep a constant current.

15. A method according to claim 14, wherein said single-stranded DNA probe comprises a sequence complementary to a sequence of said target DNA or RNA.

16. A method for the detection of a target DNA or RNA which comprises:
   (i) exposing the single-stranded DNA probe of an array according to claim 11, to a sample containing the target DNA or RNA, under hybridization conditions; and
   (ii) monitoring either the current change resulting from the hybridization process when a constant electric potential is applied between the two conducting pads or measuring the change in the electric potential required to keep a constant current.

\* \* \* \* \*